(12) United States Patent
Mauder

(10) Patent No.: US 12,077,806 B2
(45) Date of Patent: *Sep. 3, 2024

(54) METHOD FOR THE SPECTROMETRIC CHARACTERIZATION OF MICROORGANISMS

(71) Applicant: Bruker Daltonics GmbH & Co. KG, Bremen (DE)

(72) Inventor: Norman Mauder, Bremen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/303,204

(22) Filed: Apr. 19, 2023

(65) Prior Publication Data

US 2023/0250462 A1 Aug. 10, 2023

Related U.S. Application Data

(63) Continuation of application No. 17/060,766, filed on Oct. 1, 2020, now Pat. No. 11,661,620.

(30) Foreign Application Priority Data

Feb. 27, 2020 (DE) .............................. 102020105123

(51) Int. Cl.
*C12Q 1/04* (2006.01)
(52) U.S. Cl.
CPC ........... *C12Q 1/04* (2013.01); *G01N 2560/00* (2013.01)

(58) Field of Classification Search
CPC ...... C12Q 1/04; G01N 2560/00; G01N 21/65; G01N 21/3563; G01N 2021/3595; G01N 2201/1296; G01N 21/3577; G01N 27/62; G01N 2021/1748; G06N 3/04; G06N 20/00; C12M 47/02; C12M 47/16
USPC .................................................... 250/281, 282
See application file for complete search history.

(56) References Cited

U.S. PATENT DOCUMENTS 11,661,620 B2 * 5/2023 Mauder .............. G01N 21/3563
250/282

* cited by examiner

*Primary Examiner* — Michael Maskell
(74) *Attorney, Agent, or Firm* — Benoît & Côté Inc.

(57) ABSTRACT

The invention relates to a method for the spectrometric characterization of microorganisms, comprising: providing a test microorganism; acquiring spectrometric measurement data from the test microorganism under potential exposure to variance that is not based on taxonomic classification; selecting a classifier which is trained to determine the identity of a microorganism on a second taxonomic level; and applying the classifier to the measurement data in order to determine the identity of the test microorganism on the second taxonomic level, wherein the classifier is variance-conditioned in such a way that it largely or completely masks out the effect of variance in the characterization of the test microorganism on the second taxonomic level.

19 Claims, 4 Drawing Sheets

METHOD FOR THE SPECTROMETRIC CHARACTERIZATION OF MICROORGANISMS

BACKGROUND OF THE INVENTION

Field of the Invention

Figure 1A:
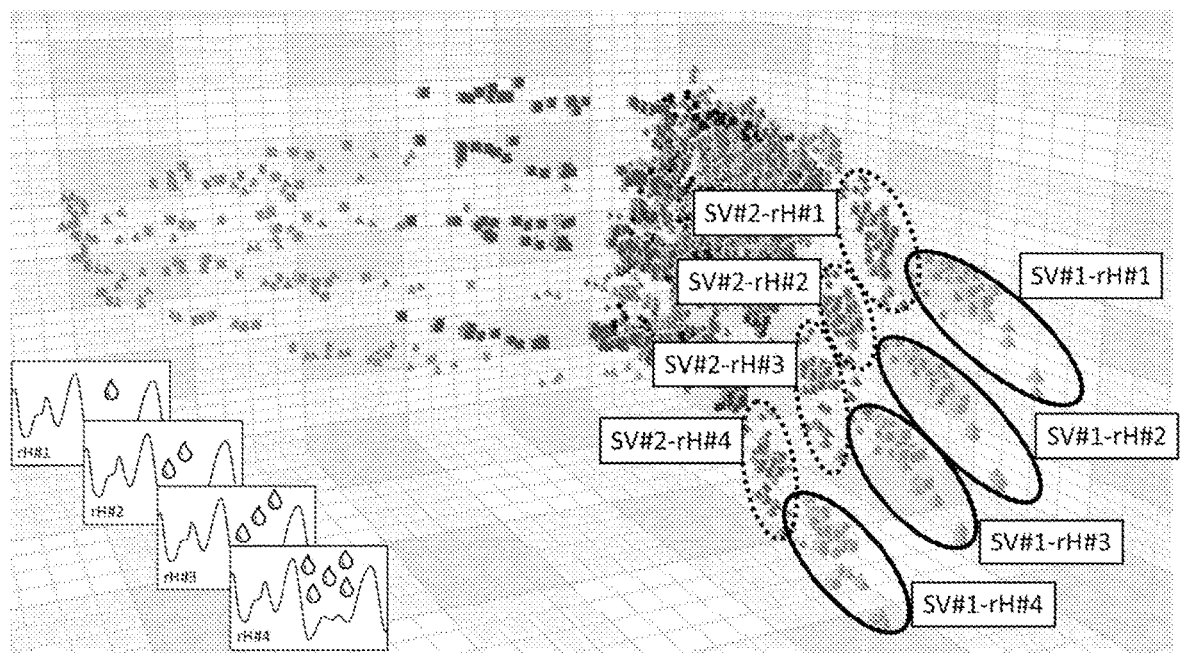

This invention relates methods for the spectrometric characterization of microorganisms, especially infrared spectrometry methods.

Description of the Related Art

The Prior Art is explained below with reference to a special aspect. This shall not be understood as a limitation, however. Useful further developments and modifications of what is known from the Prior Art can also be used above and beyond the comparatively narrow scope of this introduction, and will easily be evident to the expert skilled in the art in this field after reading the following disclosure.

During spectrometric characterization of microorganisms, e.g. bacteria, fungi, yeasts, algae or protozoa (and also viruses), the spectrometric measurements can be subject to variances outside the organism itself which affect the content of the spectra and consequently the quality of the analysis, also. Outside the organism itself means that the origins of these variances do not lie in the taxonomic classification of the microorganism.

An example can be found in infrared spectrometric characterization in the different humidity conditions which prevail during the measurement and to which the prepared samples are inevitably exposed in the measuring chamber of the infrared spectrometer because there is usually a lack of screening measures. The humidity of the samples has a direct effect on the rotational and stretching vibrations reflected in an infrared spectrum. The absolute humidity of air in the warm seasons is typically higher than in the colder seasons (seasonal dependence), for example. The humidity can also depend on the location where the measurement is taken. Consider a mobile infrared spectrometer, for example in a vehicle of an emergency management organization, which can be used at the coast (humidity tends to be high) and also in uplands or even mountains (humidity tends to be low).

This variation in humidity becomes problematic when the actual characterization measurement is carried out under conditions which differ significantly from those which prevail during the recording of reference data. When characterizing microorganisms, reference data is often used to determine the phylogenetic taxon, e.g. in the hierarchy, from top to bottom, domain, phylum, class, order, family, genus, and species. The reliability of the characterization can suffer from humidity-induced differences. The example can be transferred from the humidity to the temperature prevailing in the measurement chamber, because the temperature affects, at least indirectly, the ability of the prepared samples to absorb humidity and thus the vibrational properties of the molecules.

In the aforementioned example, instrument-based measures could be taken to mitigate the problems listed. A measurement chamber with a hermetic seal could be designed for the infrared spectrometer, or the measurement chamber could be continuously flushed with a gas which is preconditioned for humidity and temperature so that constant, uniform conditions are maintained in the chamber during the measurement. This constancy would ensure that there is no significant difference from the conditions which prevail during the recording of reference data. This hermetic sealing has not been taken up by the spectrometer manufacturers, however.

Various reports are available on the spectrometric characterization of microorganisms. Reference is made to the following documents by way of example:

US 2008/0132418 A1 explains a method for the characterization of a microorganism for the purpose of medical diagnostics or food control and environmental monitoring. At least one spectral image of the microorganism with several pixels is obtained and one or more spectra are selected from the spectral image with several pixels on the basis of predetermined spectral characteristics. The spectra selected contain spectral information characteristics of the microorganism. The identification can be performed by comparing the spectra of the selected microorganisms with spectra of reference microorganisms in a database. The database can be created by: obtaining at least one spectral image with several pixels for each of a plurality of reference microorganisms, where each pixel includes a signal which corresponds to a spectrum of a reference microorganism; and selecting spectra from the spectral images with several pixels on the basis of predetermined spectral characteristics to create the database, which contains at least one spectrum for each of the reference microorganisms.

M. J. Gupta et al. (Transactions of the ASABE, Vol. 49(4), 2006, 1249-1255) report on the identification and quantification of four enteric bacteria commonly found in food (*Escherichia* (*E.*) *coli*; colibacillus O26, *Salmonella typhimurium*, *Yersinia enterocolitica* and *Shigella boydii*) in four different food matrices with the aid of FTIR spectroscopy, from the main components derived from the infrared spectra and artificial neural networks (ANN). The classification accuracy of the ANN for the identification and quantification is given as 93.4% and 95.1%, respectively. The ANN were validated using an independent data set obtained from an enteric bacterium which was cultivated and grown separately. For such a validation, the accuracy of the ANN for the detection of *Yersinia enterocolitica* is given as between 64% and 100%. The work emphasizes the challenges of filtering the background noise in the spectra.

EP 2 174 116 B1 describes a method for the typing or identification of a microorganism by means of vibrational spectroscopy. A vibrational spectroscopy analysis is conducted on a sample of a microorganism where the signal variance caused by bleachable components in the sample is essentially eliminated from the vibrational spectra obtained. The bleachable components are identified as those which generate vibrational spectral bands exhibiting a reduction in intensity when they are photobleached. The intention is to provide corrected vibrational spectroscopy information for the purpose of typing and identification.

US 2002/138210 A1 discloses a method to compensate for drift in fingerprint spectra caused by changes in environmental factors, comprising: Culturing of a microorganism of interest and a second microorganism, which is presumed to be metabolically similar to the microorganism of interest, under a first set of environmental factors; measurement of a fingerprint spectrum of the microorganism of interest, which was cultivated under the first set of environmental factors, and a fingerprint spectrum of the second microorganism, likewise cultivated under the first set of environmental factors; detection of differences between the fingerprint spectrum of the second microorganism cultivated under the first set of environmental factors and a fingerprint spectrum of the second microorganism cultivated under a second set of environmental factors; and utilization of the differences between the fingerprint spectra of the second microorganism cultivated under the two sets of environmental factors in order to transform the fingerprint spectrum of the microorganism of interest, which was cultivated under the first set of environmental factors, into an expected fingerprint spectrum for the microorganism of interest under the second set of environmental factors.

EP 1 319 176 B1 describes a method for the characterization of spectrometer instruments according to the instrumental variation which is present between instruments, and/or the variation over time within the same instrument, comprising the steps: provision of a plurality of spectra of known standards from at least one spectrometer instrument; classification of the one or more spectrometer instruments in at least one of a plurality of predefined clusters on the basis of spectral characteristics extracted from the one or more spectra; and provision of at least one calibration model for each of the predefined clusters, with each calibration model compensating for the instrumental variation of instruments, which were classified in the respective clusters.

There is therefore a need to make spectrometric characterizations of microorganisms more robust and reliable, including in the presence of variance effects during the measurement. Further tasks that can be achieved by the invention will be immediately clear to the person skilled in the art from reading the disclosure below.

SUMMARY OF THE INVENTION

The invention relates to methods for the spectrometric characterization of microorganisms, especially infrared spectrometry methods.

Many different analytical techniques are available for the classification and identification of microorganisms, e.g. bacteria, fungi, yeasts, algae or protozoa (viruses also), but many of these are based on specific, biochemical substances which have to be extracted, modified and detected. The most frequently used are test systems which describe the properties and enzymatic activity of bacteria, e.g. bile solubility, catalase, coagulase, DNase, motility, toxins, optochin, Streptex, oxidase, Gram staining, Ziehl-Neelsen staining, spores, casings, fermentation capabilities, etc. Other frequently used methods are cellular fatty acid analysis, protein profiling, polymerase chain reaction (PCR) and 16S rRNA-gene sequencing, total DNA G+C content, high-resolution gas/liquid chromatography and microscopy to determine the cell morphology on the basis of a difference in shape and appearance. What all the aforementioned methods have in common is that they use only one specific marker of the bacteria for classification. Infrared spectrometry, in contrast, detects all biomolecules present in a bacteria cell simultaneously, since almost every biomolecule absorbs infrared radiation. The spectral information resulting from the interaction between infrared radiation and biomolecule includes all the cellular components, and can therefore be used as an almost complete phenotypical description of the bacteria analyzed.

A test microorganism is provided whose identity is known on a first taxonomic level. The identity of the test microorganism on the first taxonomic level can particularly be determined in advance by at least one of the following methods: (i) mass spectrometry, (ii) infrared spectrometry, (iii) growth on selective media ("API (Analytical Profile Index) test") and (iv) gene sequence analyses. An example of determining the prior knowledge can be found in DE 10 2013 022 016 B4, where in particular a mass spectrometric determination of the species of a microorganism is supplemented with an infrared spectrometric determination of the subspecies. The method can, furthermore, involve isolating the test microorganism from a habitat, e.g. a biological and/or chemical matrix. The isolating of the test microorganism preferably comprises the removal of the matrix, e.g. by washing, filtering, centrifuging off, evaporating, extracting, sedimenting and/or other forms of separation. Provision of the test microorganism can, moreover, include a multiplication step, e.g. incubation in a nutrient solution or on a flat nutrient medium such as Agar.

The test microorganism is preferably sterilized. The sterilization method can comprise exposing the test microorganism to a metabolism-inhibiting liquid, e.g. an alcohol such as ethanol or isopropanol, or an acid such as formic acid, and/or exposure to an energy source, e.g. heat or high-energy radiation (possibly ultraviolet light). Sterilization means, in particular, that the microorganism loses its ability to multiply even under favorable conditions in order to prevent the biological risks associated with inadvertent/uncontrolled spread occurring in an analytical laboratory. In certain circumstances it may not be necessary to sterilize the test microorganism, for example when working in an analytical laboratory with a biosafety level of 2 or higher, because it is safe to assume that the specialist staff working there are sufficiently trained.

Spectrometric measurement data is acquired from the, possibly sterilized, test microorganism under conditions which allow the influence of at least one source of variance which does not originate from the taxonomic classification of the test microorganism. The one or more variances can be atmospheric in origin and comprise, in particular, different values on at least one of the following scales: temperature, humidity, pressure, and carbon dioxide content of the ambient air. A variance of atmospheric origin or atmospheric variance manifests itself in changes in the conditions close to and around a test microorganism sample prepared for a spectrometric measurement, usually prepared on a specimen slide, e.g. a small glass plate. The one or more variances preferably relate to changes which can be influenced on a continuous and finite scale, in particular those which are limited at one end at least, e.g. absolute zero for temperature, or which have a lower and upper limit, e.g. 0% to 100% for relative humidity.

A classifier is selected which has been trained to determine the identity of a microorganism on a second taxonomic level, which is subordinate to the first taxonomic level. Possible identities of the classifier on the second taxonomic level are assigned to the known identity of the test microorganism on the first taxonomic level. The first and second taxonomic levels can be direct neighbors, e.g. species and subspecies, respectively. Furthermore, the first taxonomic level may correspond to the species and the second taxonomic level may include different varieties, e.g. pathogenic and non-pathogenic varieties, resistant and susceptible varieties, or different strains of the species. These varieties/strains of different types can be grouped into identity subclasses for the purpose of characterization, e.g. all pathogenic serotypes/strains in a first group and all non-pathogenic serotypes/strains in another group, which is distinct from the first group.

The term serotype or serovar (short for serovariety) is used to describe varieties within subspecies of bacteria which can be differentiated by means of serological tests. They differ in respect of the antigens on the surface of the cells and are identified in conventional microbiology by means of specific antibodies. The taxonomic hierarchy for serotypes is as follows: genus⇒species⇒subspecies (subsp.)⇒serotype, for example with the added binomial species name *Salmonella enterica* subsp. *enterica* serotype *typhi*, short form *Salmonella typhi*.

A pathovar (from the Greek pathos "disease") is a bacterial strain or group of strains with the same characteristics whose pathogenicity allows them to be differentiated from other strains within the species or subspecies. Pathovars are designated by means of a third or fourth addition to the binomial species name. The bacterium *Xanthomonas axonopodis*, for example, which can cause citrus canker, has various pathovars with different host specializations: *X. axonopodis* pv. *citri* is one of them. The abbreviation "pv." stands for "pathovar". The virulent strains of human pathogens also have pathovars, but in this case they are designated by prefixes in front of the name. The mostly completely harmless intestinal bacterium *Escherichia coli*, for example, has the highly dangerous pathovars enterohemorrhagic *E. coli* (EHEC), enteropathogenic *E. coli* (EPEC), enterotoxigenic *E. coli* (ETEC), enteroinvasive *E. coli* (EIEC), enteroaggregative *E. coli* (EAEC) and diffusely adherent *E. coli* (DAEC). The pathovars, in turn, can comprise different serotypes: EHEC, for example, has many known serotypes. Around 60 percent of all identified EHEC serotypes are O157, O103 and O26. The sero-subtype O157/H7 is particularly dangerous.

In a broader sense, the characterization of microorganisms can also encompass varieties which differ in terms of other medically relevant properties, in particular resistance to antimicrobial substances such as antibiotics (especially beta-lactam antibiotics and glycopeptide antibiotics) and also antimycotics, but also in terms of toxin formation ("toxivars") or susceptibility to the same or similar bacteriophages ("phagovars"). In general, the term "biovars" is used if a selection of microorganisms of a species or subspecies have biological characteristics in common. An example of an antibiotic-resistant variety is MRSA: methicillin-resistant *Staphylococcus aureus*.

The term "strain" describes a population which was grown from a single organism and is kept at a (often state-run) depository for microorganism strains. An internationally standardized strain designation is added to the nomenclature chain comprising genus, species, subspecies and variety. The individual organisms of a strain are genetically identical; different strains vary slightly in their genetic make-up.

The classifier is applied to the measurement data to determine the identity of the test microorganism on the second taxonomic level. The classifier is also variance-conditioned, since it is obtained by training it on targetedly variance-loaded spectrometric reference data of different, known reference microorganisms which exhibit the same identity as the test microorganism on the first taxonomic level and cover different identities on the second taxonomic level. This training includes the stipulation of giving greater weighting to those spectral characteristics of a first type from the reference data which assist the differentiation of the different identities on the second taxonomic level than to those spectral characteristics of a second type from the reference data which are affected by the targeted variance in order to largely or completely mask out the effect of variance in the characterization of the test microorganism on the second taxonomic level.

In a further aspect of the invention, for the purpose of distinguishing identities of a microorganism on a predetermined taxonomic level, a classifier conditioned with respect to at least one variance is applied to spectrometric measurement data acquired from a (optionally sterilized) test microorganism under conditions which allow the one or more variances to have an effect. The one or more variances do not have their origins in the taxonomic classification of the microorganism.

Specialists in the field will recognize that all the embodiments disclosed in connection with the method can also be transferred to the application.

BRIEF DESCRIPTION OF THE DRAWINGS

The invention can be better understood by referring to the following illustrations. The elements in the illustrations are not necessarily to scale, but are primarily intended to illustrate the principles of the invention (mostly schematically):

FIG. 1A shows a principal component analysis (PCA) in a three-dimensional space of infrared spectra of different serotypes (SV) of *Streptococcus pneumoniae* as a function of a varying relative humidity (rH).

FIG. 1B shows the evaluation of the same spectra as in FIG. 1A, but by means of a linear discriminant analysis directed at removing the influence of the varying humidity in the spectral characteristics.

FIG. 2 shows a greatly simplified diagram of the measurement setup of a Fourier transform infrared spectrometer (FT-IR) in transmission with acquired spectrum.

FIG. 3 shows an example sequence of steps in the preparation of a spectrometric microorganism sample before the measurement (counterclockwise).

FIG. 4 shows a principal component analysis (PCA) in a two-dimensional space of infrared spectra of different serotypes (SV) of *Legionella pneumophila* as a function of a varying relative humidity (rH), where the serotypes are grouped by pathogenicity.

DETAILED DESCRIPTION

While the invention has been illustrated and explained with reference to a number of embodiments, those skilled in the art will recognize that various changes in form and detail can be made without departing from the scope of the technical teaching, as defined in the enclosed claims.

FIG. 1A shows a principal component analysis (PCA) of infrared spectra of different serotypes (SV) of the microorganism *Streptococcus pneumoniae* as a function of four different humidity levels between 10% and 80% relative humidity (rH #1 to rH #4), which were set specifically for the measurement in the measurement chamber of the infrared spectrometer. As is to be expected, the individual accumulations of data points are spread over the serotypes. In FIG. 1A, the four resulting data clouds of two example serotypes are emphasized with differently chain-dotted ovals (SV #1 and SV #2) for the sake of clarity. The measurements were each based on several strains/isolates of one serotype, as reflected in the elongated data clouds for the individual humidity levels. The different strains/isolates are labeled by means of different shapes such as pyramids, cubes and spheres. In addition, the separation of the measurements of the same serotype for the different humidity levels is clearly visible. Surprisingly, it is also apparent that the humidity dependence of the spectral characteristics does not cause data clouds of different serotypes to merge into one another and/or become mixed up. Instead, the individual data clouds of the different serotypes remain separate ("stratified"), including for different humidity levels, and can therefore be distinguished in the course of a characterization.

This finding gave reason to assume that this property of stable distinguishability even when the variance during a spectrometric measurement is considerable (10% to 80% on the humidity scale) can be used to eliminate this variance in the characterization by means of advanced evaluation methods, such as methods of machine learning, and thus to obviate the need for complex conversions of the spectrometers used for this purpose.

The spectra on which the diagram in FIG. 1A is based were accordingly evaluated a second time. A linear discriminant analysis was used with the specified purpose of identifying and increasing the weighting of those spectral characteristics, e.g. principal components, which maximize the distinctiveness of the individual, known serotypes, whereas those spectral characteristics which are influenced by the variances within the individual serotype classes, which essentially originate from the different strains (albeit a variance within the organism) and humidity levels during the measurement, were to be masked out as much as is possible.

Figure 1B:
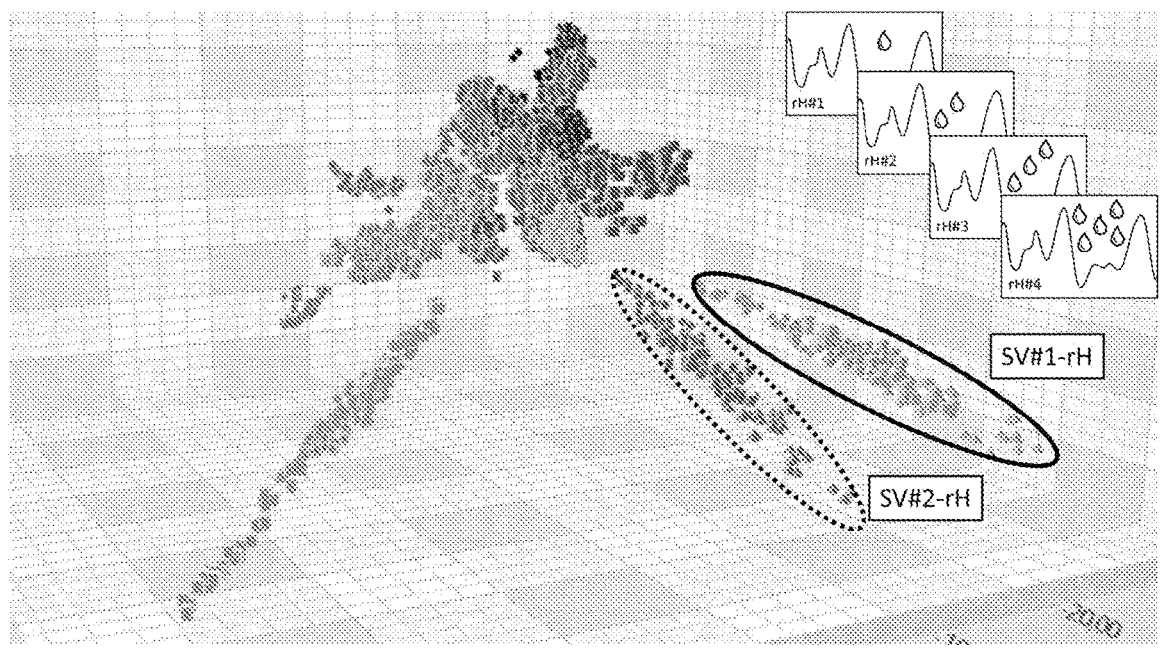

The result is shown in FIG. 1B. As can be seen, the four different humidity levels, as manifested in FIG. 1A in a stratum of four clearly separate data clouds per serotype, were merged, regardless of humidity, into one continuous, spindle-shaped data cloud per serotype, without causing the individual serotype data clouds to become superimposed or overlapping each other. This result can be used to create a variance-conditioned classifier, which—when it is applied to a new spectrum of *Streptococcus pneumoniae* with yet unknown serotype—can assign the newly determined spectral characteristics to the known spatial volumes. To this end, the volumes of the multi-dimensional feature space, which underly the data clouds, can be marked out and an examination is carried out to ascertain which volume of the feature space is the one into which the important spectral characteristics of a new spectrum are projected.

Figure 2:
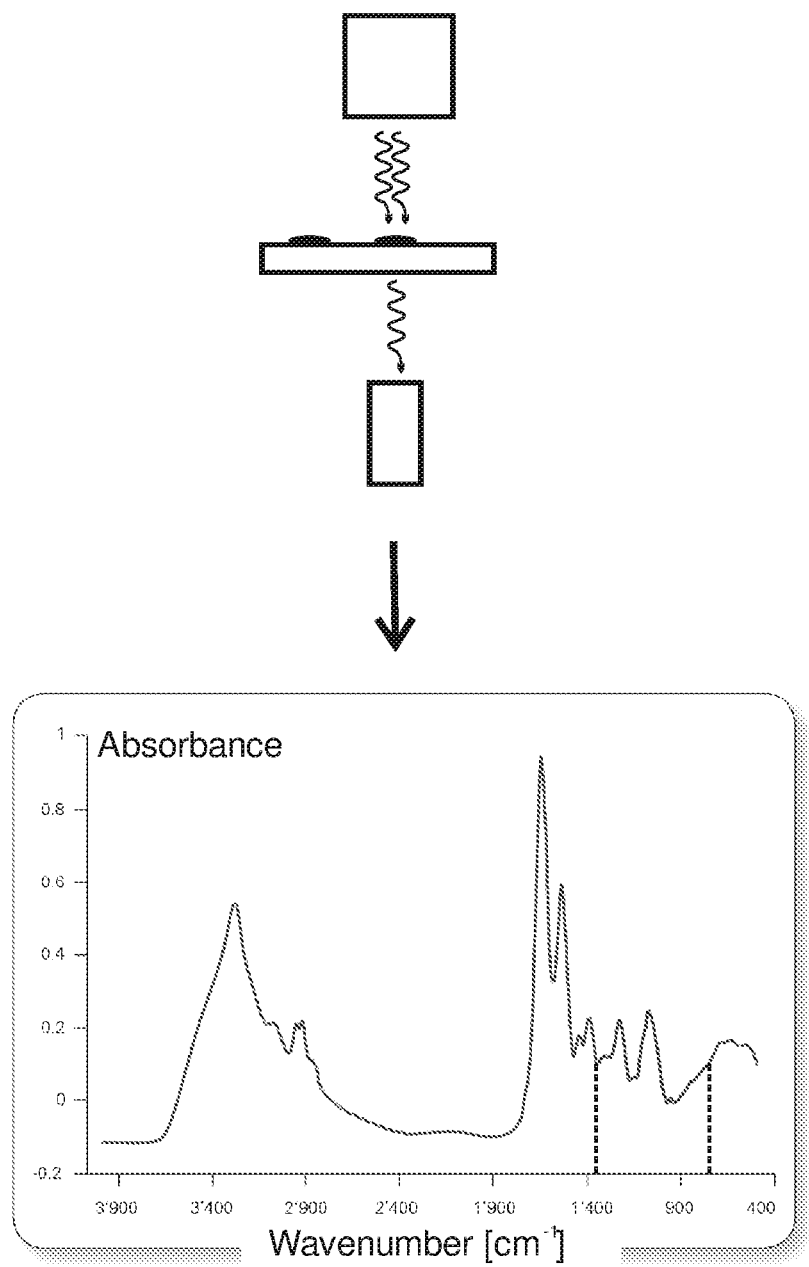

For an infrared spectrometric characterization measurement in transmission, a Fourier transform spectrometer (FT-IR), which provides a high resolution, can be used. See diagram of the measurement setup in FIG. 2. The spectra are typically measured from 4000 cm$^{-1}$ to 500 cm$^{-1}$. The area highlighted in FIG. 2 (bottom) with a broken line between around 1350 cm$^{-1}$ and around 700 cm$^{-1}$ is deemed to be particularly productive for the spectral specificity. Several hundred spectra are measured and summed at acquisition rates of twenty spectra per second in order to improve the signal-to-noise ratio.

The infrared spectra are based on thousands of vibrations of the functional groups and the polar bonds in the biological material; these in turn originate from all the components of the microorganism cells, such as DNA, RNA, proteins, internal structures, membranes, and cell walls, through to energy stores. There are no obvious assignments of molecules to individual characteristics in the spectra, even though certain spectral ranges can be preferentially assigned to certain molecular species: the fatty acid range from 3050 to 2800 cm$^{-1}$ with vibrations of the $CH_2$ and $CH_3$ groups, the amide range from 1750 to 1500 cm$^{-1}$ with peptide bonds, the polysaccharide range from 1200 to 900 cm$^{-1}$. The range from 900 to 700 cm$^{-1}$ is sometimes called the fingerprint range because it contains something from all molecules and is very important for differentiating between the varieties.

In a slightly modified embodiment, the infrared spectra can also be measured in reflected light. In this case they are prepared on a metallically reflective substrate made of aluminum, for example. It is also possible to use Raman spectroscopy, which has the advantage that the spectra of the prepared microorganisms can also be measured in liquids, and also require much smaller quantities of sample material.

The knowledge gained from FIGS. 1A and 1B can be implemented to create a variance-conditioned classifier as per the steps below:

(i) Prepare the Reference Microorganisms and Specify the Variance(s).

The first task is to specify the classes to be distinguished. If knowledge of the species, e.g. *Streptococcus pneumoniae*, as the identity on the first taxonomic level is assumed, the objective can be to determine the corresponding serotypes as possible identities on the second, subordinate taxonomic level. As an example, the 23 serotypes of *Streptococcus pneumoniae* which are found most frequently in clinical tests can be selected. The reference biomass of these microorganisms can be obtained from the publicly operated depositories such as the Leibniz Institute DSMZ—German Collection of Microorganisms and Cell Cultures GmbH in Braunschweig.

To give adequate consideration to the variance within the organism, a representative selection of microorganisms of the classes to be distinguished can be taken into account. Depending on availability, this can be three to six different strains per serotype in the example of *Streptococcus pneumoniae*; in the case of the 23 most common serotypes, 69 to 138 strains could be used for compiling the reference data and creating the classifier.

The next task is to specify the parameter whose variance is to be imposed on the recording of the reference data and whose variable occurrence during an infrared spectrometric measurement appears possible. This can be an atmospheric variance, e.g. humidity, pressure, gas concentration or temperature. In principle, more than one variance parameter can be taken into account when recording the reference data, for example both humidity and temperature. However, broader coverage in respect of the conceivable variances is also associated with a corresponding increase in the work required to measure the reference data, since the different representative values or reference values of the variance parameters have to be recorded in combination with each other. A list of reference points of the variance parameter(s) is selected which cover all realistic conditions during a spectrometric measurement. It should be possible to interpolate between the values of this representative selection of reference points.

(ii) Recording the Reference Data

First the strains of the reference microorganisms can be prepared in a standardized way. For example, after incubation on or in a suitable culture medium and, if necessary, after being sterilized to prevent biological contaminations, they can be deposited on a specimen slide for infrared spectrometry in several replicates and then introduced into the measurement chamber. The measurement chamber is maintained at a constant, predetermined value in respect of the variance parameter(s), for example 10% relative humidity at 20° C. After the specimen slide is introduced, it is preferable to wait a certain length of time, e.g. five to ten minutes, so that the prepared biomass of the reference microorganisms can become acclimatized to the preset conditions.

After all the parameters have settled, the reference data of the prepared reference microorganisms can be recorded under the preset conditions. This procedure is repeated under the appropriately varied conditions, i.e. for example at 30%, 55% and 85% relative humidity and constant 20° C. Each change in the variance value should be followed by an acclimatization period of several minutes to allow the transient processes to decay and to obtain reproducible stable results.

This method of recording reference data can be supplemented by measurements of subordinate variances, which result, for example, from slightly different incubation conditions (biological replicates), or preparation conditions (e.g. technical replicates, use of different batches of reagents/agents or chemicals), or from measurements taken on different spectrometers to allow for instrumental variances. The reference data thus recorded is checked for completeness, obvious outliers (e.g. using methods of Local Outlier Factoring, LOF), and/or plausibility, and are corrected and/or re-recorded, where necessary.

(iii) Training of the Variance-Conditioned Classifier

It is preferable to use methods of machine learning, e.g. artificial neural networks (ANN) or linear discriminant analyses (LDA). In respect of the class affiliation, e.g. serotype #1, serotype #2, . . . , serotype #23 in the previously described example of *Streptococcus pneumoniae*, the training is supervised. Regarding the variance conditions, i.e. different ambient conditions (e.g. humidity) or other influencing factors (e.g. varying incubation, preparation, spectrometer), the training of the classifier is unsupervised, however. This is equivalent to the requirement to emphasize the significance of those spectral characteristics in the reference data which maximize the distinctiveness of the individual classes (here serotypes of the species *Streptococcus pneumoniae*), whereas those spectral characteristics which are strongly influenced by the variances have a lower weighting and are thus virtually masked out. The spectral characteristics can manifest themselves in the principal components, for example.

In simple terms, and for the purpose of illustration (without any claim to strict scientific correctness), the machine learning algorithm identifies those partial volumes in a usually multi-dimensional, multivariate feature space which are each to be assigned to one of the classes distinguished (i.e. identities on the second taxonomic level). An unexpected aspect of this basically known method of taking interferences into account was that atmospheric variances such as relative humidity do not cause the spectral characteristics of one serotype/strain to overlap with those of other serotypes/strains when the humidity varies, but instead they remain separate, and thus ensure distinguishability in a space of spectral characteristics, also under such varying conditions.

As is usual in such training phases which use reference data, there is the option to test the efficiency of the resulting classifier by means of a cross-validation. If appropriate, the machine learning algorithm can be adjusted on the basis of the results of the cross-validation in order to further improve the accuracy of the classifier.

(iv) Validation (Optional)

When the taxonomic assignment of one or more test microorganisms is known, a validation test run can be conducted under conditions which permit the expected variance (e.g. varying relative humidity) in order to verify the efficiency on the basis of external data.

This procedure for creating a classifier can be repeated to create a variance-conditioned classifier database with a very wide range of microorganisms, which in turn can be identified on different taxonomic levels. Reference data can preferably be acquired and processed from pathogens which occur in the clinical environment with the greatest frequency.

Figure 3:
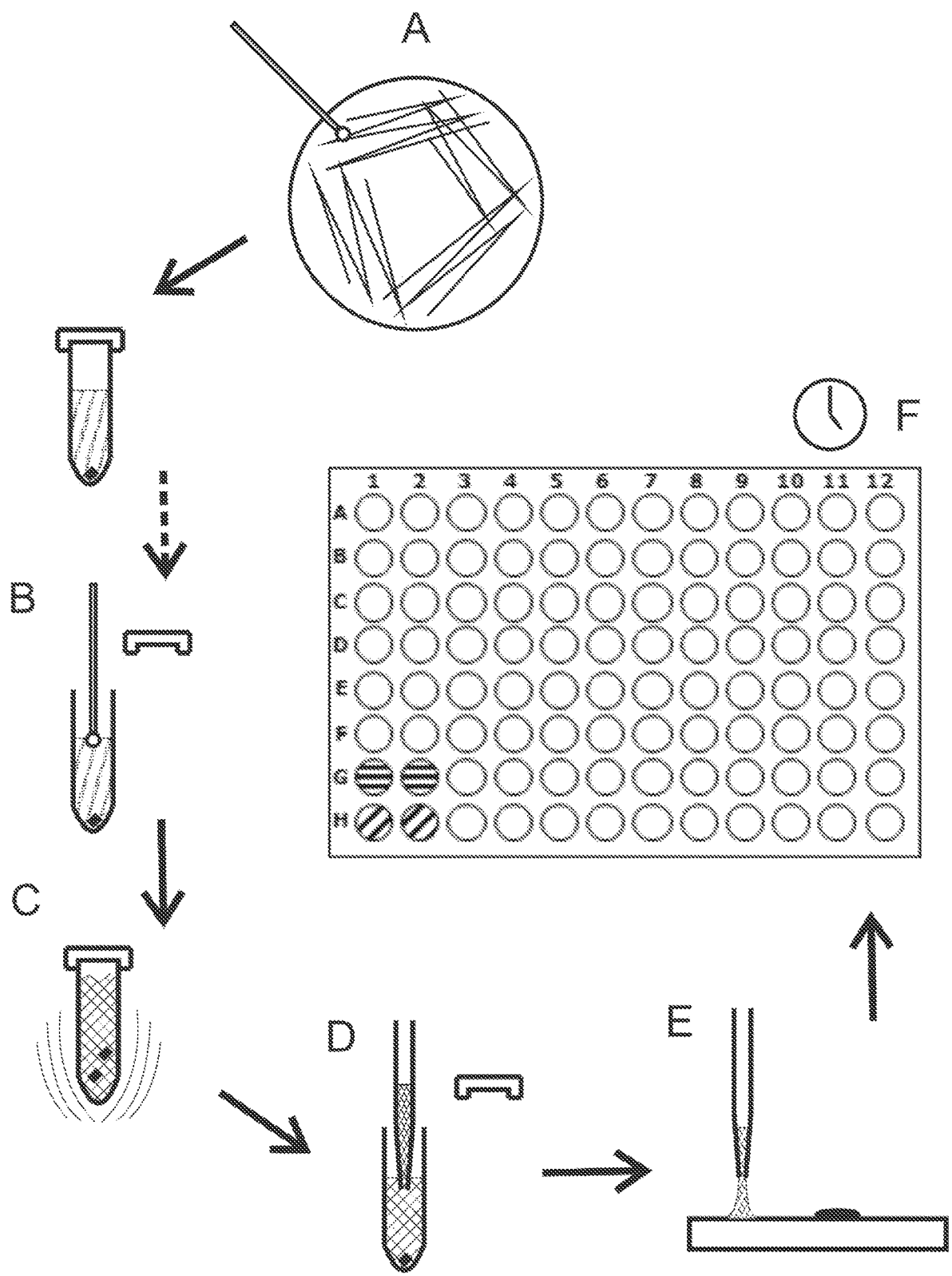

After the variance-conditioned classifier is created, the method for characterizing a microorganism can be conducted as follows, see the schematic sequence in FIG. 3:

First, the identity of the test microorganism must be known or must have been determined on the first taxonomic level, e.g. the species, using a mass spectrometer such as the MALDI Biotyper® (Bruker Daltonik GmbH, Bremen, Germany). On this basis, the variance-conditioned classifier that is appropriate for the identity determined is selected. By way of example, attention is drawn in this context to the method described in EP 3 083 981 A1.

To obtain sufficient biomass, the test microorganism can be incubated in a nutrient solution or on a flat nutrient medium. The microorganism cells thus grown can then be removed from the nutrient medium, for example by separating them from the nutrient solution, e.g. by centrifuging or filtering, or by sampling from an agar plate. For the purpose of sterilization, the microorganisms thus harvested can be re-suspended in an activity-inhibiting liquid such as ethanol (e.g. 70% v/v).

Microorganisms react very sensitively to changes in growth conditions, such as different media, temperatures, nutrients, changes in the gas supply (oxygen and others), moisture, incubation period etc. These factors can bring about changes in cell composition and in metabolism, which can be detected with infrared spectrometry. For the purpose of incubation, the cell material of a pure single colony can be spread onto an agar plate using a spatula in order to bring about confluent growth. This technique enables the sampling of cells in a very reproducible mixture of the different growth phases which are always present in colonies. For most clinically relevant strains, the optimum incubation period is around 16 to 24 hours, and the incubation temperature frequently used for bacteria is around 35° C. to 37° C. The sample material of an incubated test microorganism can be harvested directly from the center of the cell layer e.g. using a calibrated platinum loop with a diameter of one millimeter (step A).

When the test microorganism is grown on a flat nutrient medium such as agar, biomass can be sampled from one or more colonies and deposited directly on a spectrometric specimen slide. It is important to ensure uniform distribution, with the option to sterilize the biomass by irradiating it with ultraviolet light (e.g. in the case of *Streptococcus pneumoniae*). Alternatively, the biomass can likewise be re-suspended in a metabolism-inhibiting liquid (step B). The liquid can also be de-ionized water, which does not usually exert any metabolism-inhibiting effect. In this case also, the test microorganism can be sterilized by ultraviolet radiation or other energy source (e.g. heat) after being deposited on a test site of a specimen slide.

Care must be taken that no residues of the nutrient medium, which could interfere with the measurement result, adhere to the test microorganism taken out of or from the nutrient medium. To achieve uniform distribution of the biomass of the test microorganism in the suspension, small cylinders or beads of reaction-inert material such as steel can be added to the suspension and the sealed suspension vessel can then be shaken (step C). The suspension is then aliquoted and applied gently e.g. by means of a pipette with a plastic tip, onto the specimen slide in replicates (step D), whose number may vary from protocol to protocol. Uniform application with homogeneous layer thickness promises the best measurement results (step E). After all samples under investigation have been applied to the specimen slide, it is left to stand for several minutes, e.g. ten to thirty minutes, at a specified temperature, e.g. 37° C., for the suspensions to dry (step F). If the test microorganism is applied to the specimen slide as soon as it is harvested from the incubation vessel without any further re-suspension, the drying can be omitted completely, or at least it can be made much shorter.

The specimen slides thus prepared can then be introduced into a measurement chamber of a spectrometer and measured sample by sample under conditions which allow the influence of at least one source of variance. Several positions on the specimen slide can also be coated with test standard biomass to check the technical performance of the spectrometer, for example in line with the applicant's method explained in EP 3 392 342 A1.

The spectra recorded can be subjected to an analysis with the variance-conditioned classifier created in advance after the usual processing steps, such as baseline subtraction, smoothing and calculation of the second derivative. As described above, only (or at least predominantly) those spectral characteristics that are not influenced by the variance, or only to a slight degree, are taken into account here, whereas those spectral characteristics which exhibit a high variance-induced variation are largely or completely masked out.

Processing the measurement data with the variance-conditioned classifier leads to the spectrum under investigation being assigned to one of the possible identities on the second taxonomic level. In the example of *Streptococcus pneumoniae*, this means one of the referenced serotypes. Only in rare cases is a reliable characterization not possible, for example because of unforeseen disturbances during the incubation, sample preparation or measurement, or because the identity of the test microorganism sought on the second taxonomic level is not included in the reference data (e.g. in the case of a very rare serotype which is of almost no relevance in clinical practice).

Figure 4:
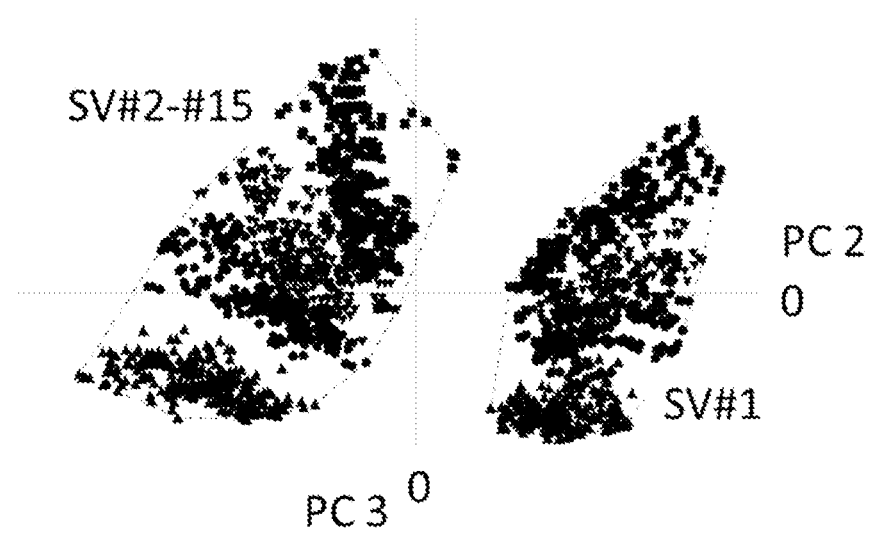

FIG. 4 shows a further example of the continuing distinguishability of serotypes even under varying levels of humidity in a principal component space, which is shown in two dimensions here for the sake of clarity (PC 2, PC 3). The basis is the species *Legionella pneumophila*, of which fifteen serotypes are taken into account in the illustration of spectral characteristics. The serotypes are not individually classified, however, but grouped into strongly pathogenic and less pathogenic serotypes. This distinguishes the first serotype SV #1 (data cloud on the right), which is responsible for 70 to 80 percent of all legionellosis in humans, from the next fourteen SV #2 to SV #15, which are much less pathogenic, if at all. Similarly, it would also be possible to classify susceptible (sensitive) and resistant serotypes/strains together in groups.

The reference data of the different serotypes of the reference microorganisms *Legionella pneumophila*, whose underlying strains are coded with different symbols such as triangles, squares and circles, were acquired under four different relative humidities (arid 10%, semi-arid 30%, humid 55% and tropical 85%). In the diagram, this variance essentially manifests itself in the elongation of the data clouds along the principal component axis PC 2. However, it is clear that, irrespective of the variance, the data cloud belonging to serotype 1 (SV #1), is sufficiently removed from the grouped data cloud of the other serotypes SV #2 to SV #15 to ensure the distinguishability on the basis of spectral characteristics. If a clinic experiences an increase in the number of cases of diarrhea which can be ascribed in a first analysis, for example with the established mass spectrometric MALDI-TOF method, to the bacterial species *Legionella pneumophila*, an appropriately trained classifier can be used in the subsequent infrared spectrometric analysis of the isolated and incubated pathogen to distinguish the particularly pathogenic serotype SV #1 from the other less dangerous serotypes SV #2 to SV #15 in order to start a specific treatment in the case of a positive result. This procedure can of course be transferred to other microorganisms. The flexibility of the classifier creation described here is boundless.

Starting from the afore-described methods, variance-conditioned classifiers are determined for a plurality of possible micro-organisms and also for a plurality of possible sources of variance, individually and also several in combination, during a spectrometric measurement. With knowledge of the identity of a microorganism to be characterized on a first taxonomic level, a spectrometric sub-characterization of the identity on a second subordinate taxonomic level can thus be robustly and reliably carried out by selecting the appropriate variance-conditioned classifier.

Further embodiments of the invention are conceivable in addition to the embodiments described by way of example. With knowledge of this disclosure, those skilled in the art can easily design further advantageous embodiments, which are to be covered by the scope of protection of the claims, including any equivalents as the case may be.

The invention claimed is:

1. A test system for a spectrometric characterization of microorganisms, comprising:

a mass spectrometer for determining an identity of a test microorganism on a first taxonomic level;

an infrared spectrometer having a measurement chamber in which a specimen slide carrying biomass of the test microorganism is held during the acquisition of infrared spectrometric measurement data from the test microorganism; and a processing device having access to a database which includes a plurality of variance conditioned classifiers, each classifier being trained to determine the identity of the test microorganism on a second taxonomic level which is subordinate to the first taxonomic level, where possible identities of the classifier on the second taxonomic level are assigned to an identity of the test microorganism on the first taxonomic level, and further each classifier being conditioned with respect to at least one variance, for the purpose of distinguishing identities of a microorganism on the second taxonomic level, to infrared spectrometric measurement data acquired from the test microorganism under conditions which allow the at least one variance to have an effect, wherein the at least one variance does not have its origin in the taxonomic classification of the microorganism;

wherein the processing device selects a classifier from the database in accordance with the determined identity of the test microorganism on the first taxonomic level and applies it to the infrared spectrometric measurement data acquired from the test microorganism in order to determine its identity on the second taxonomic level.

2. The test system of claim 1, wherein the mass spectrometer is of a MALDI Biotyper® type.

3. The test system of claim 1, wherein the test microorganism is taken from among the group including: bacteria, fungi, yeasts, algae, protozoa, viruses.

4. The test system of claim 1, wherein the first taxonomic level corresponds to a species.

5. The test system of claim 1, wherein the second taxonomic level corresponds to a subspecies.

6. The test system of claim 1, wherein the infrared spectrometer is of a Fourier transform type.

7. The test system of claim 1, wherein the infrared spectrometer is of a Raman type.

8. The test system of claim 1, wherein the infrared spectrometer operates in transmission.

9. The test system of claim 8, wherein the specimen slide comprises a glass plate.

10. The test system of claim 1, wherein the infrared spectrometer operates in reflection.

11. The test system of claim 10, wherein the specimen slide comprises a metallically reflective substrate.

12. The test system of claim 11, wherein the metallically reflective substrate comprises aluminum.

13. The test system of claim 1, wherein the at least one variance is of atmospheric origin.

14. The test system of claim 13, wherein the at least one variance contains different values on at least one of the following scales: temperature, humidity, pressure, and carbon dioxide content of ambient air.

15. The test system of claim 1, wherein the classifiers in the database are obtained and trained with the aid of one or more methods of machine learning.

16. The test system of claim 15, wherein said methods of machine learning comprise at least one of artificial neural networks (ANN) and linear discriminant analyses (LDA).

17. The test system of claim 1, wherein the at least one variance relates to changes which can have influence on a continuous and finite scale.

18. The test system of claim 17, wherein the at least one variance is limited at one end at least.

19. The test system of claim 18, wherein the at least one variance has a lower and an upper limit.

* * * * *